(12) United States Patent
Meyer-Schwickerath

(10) Patent No.: US 11,659,993 B2
(45) Date of Patent: May 30, 2023

(54) METHOD FOR DETERMINING THE OCCURRENCE OF A VASCULAR COLLAPSE OF A BLOOD VESSEL IN OR AT THE EYE AS WELL AS A HOLDING DEVICE AND AN OPHTHALMODYNAMOMETRY ASSEMBLY

(71) Applicant: I-DYNAMOMETER GMBH, Bocholt (DE)

(72) Inventor: Rolf Meyer-Schwickerath, Bocholt (DE)

(73) Assignee: I-DYNAMOMETER GMBH, Bocholt (DE)

( * ) Notice: Subject to any disclaimer, the term of this patent is extended or adjusted under 35 U.S.C. 154(b) by 1008 days.

(21) Appl. No.: 16/473,728

(22) PCT Filed: Dec. 29, 2017

(86) PCT No.: PCT/EP2017/025374
§ 371 (c)(1),
(2) Date: Jun. 26, 2019

(87) PCT Pub. No.: WO2018/121886
PCT Pub. Date: Jul. 5, 2018

(65) Prior Publication Data
US 2020/0170505 A1    Jun. 4, 2020

(30) Foreign Application Priority Data

Dec. 30, 2016  (DE) .................... 10 2016 015 577.9
Feb. 22, 2017  (DE) .................... 10 2017 001 677.1
Oct. 6, 2017   (DE) .................... 10 2017 123 241.9

(51) Int. Cl.
*A61B 3/12*    (2006.01)
*A61B 3/10*    (2006.01)
(Continued)

(52) U.S. Cl.
CPC ............ *A61B 3/1241* (2013.01); *A61B 3/102* (2013.01); *A61B 5/0053* (2013.01);
(Continued)

(58) Field of Classification Search
CPC ..... A61B 3/1241; A61B 3/102; A61B 5/0053; A61B 5/02007; A61B 5/0261; A61B 5/6803; A61B 3/16
(Continued)

(56) References Cited

U.S. PATENT DOCUMENTS

2002/0049389 A1* 4/2002 Abreu ............... G02C 7/04
                                              600/318
2004/0064057 A1* 4/2004 Siegel .............. A61B 3/1241
                                              600/500
(Continued)

FOREIGN PATENT DOCUMENTS

EP        0161018 A1    11/1985

OTHER PUBLICATIONS

Ethier, C. Ross, et al. "Ocular Biomechanics and Biotransport" Annu. Rev. Biomed. Eng. 2004. vol. 6, pp. 249-273; Feb. 6, 2004.
(Continued)

*Primary Examiner* — Mohammed A Hasan
(74) *Attorney, Agent, or Firm* — Jason H. Vick; Sheridan Ross, PC

(57) ABSTRACT

The invention relates to a method for determining the occurrence of a vascular collapse of a blood vessel in or on the eye. According to the invention, it is proposed that the vascular collapse be determined from a measured temporal change of blood flow in the blood vessel.

20 Claims, 8 Drawing Sheets

Figure 1:
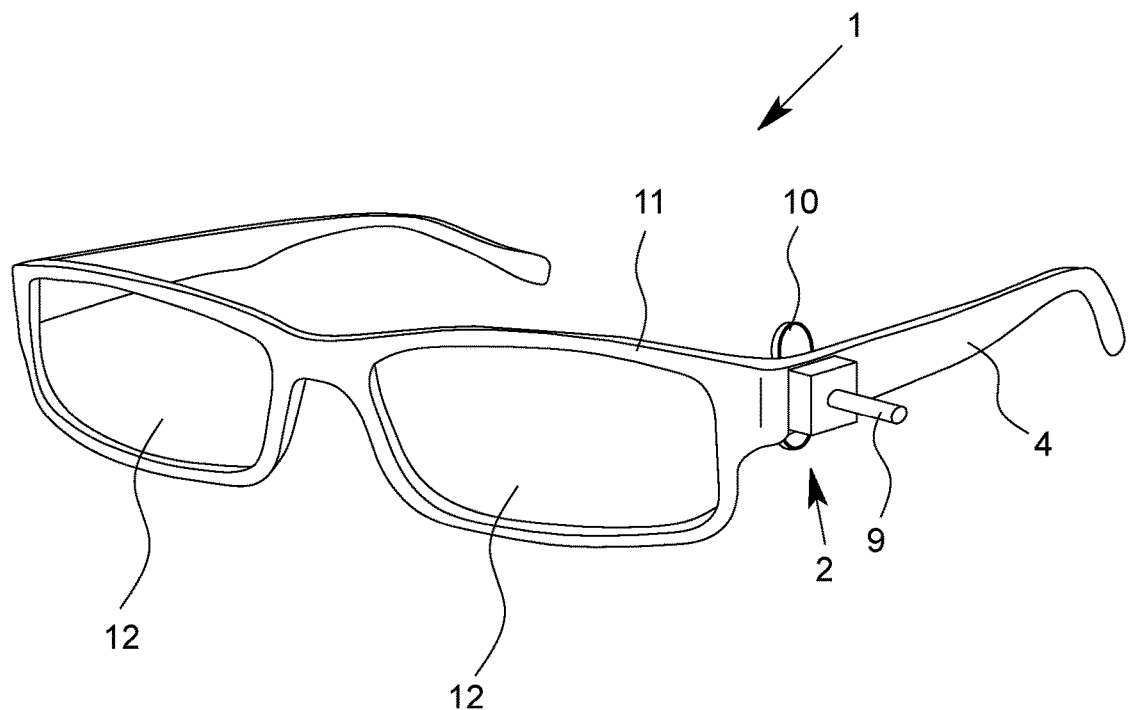

(51) Int. Cl.
*A61B 5/00* (2006.01)
*A61B 5/02* (2006.01)
*A61B 5/026* (2006.01)

(52) U.S. Cl.
CPC ........ *A61B 5/02007* (2013.01); *A61B 5/0261* (2013.01); *A61B 5/6803* (2013.01)

(58) Field of Classification Search
USPC ........................................................ 600/427
See application file for complete search history.

(56) References Cited

U.S. PATENT DOCUMENTS

| | | |
|---|---|---|
| 2004/0186367 A1 | 9/2004 | Fresco |
| 2004/0230124 A1 | 11/2004 | Querfurth |
| 2007/0024946 A1* | 2/2007 | Panasyuk ............... A61B 5/416 359/253 |
| 2010/0152565 A1 | 6/2010 | Thomas et al. |
| 2010/0331684 A1* | 12/2010 | Ragauskas ............... A61B 8/06 600/438 |
| 2013/0144185 A1 | 6/2013 | Fuller et al. |
| 2016/0262625 A1* | 9/2016 | Lawrenson .......... A61B 5/0077 |

OTHER PUBLICATIONS

Invitation to Pay Additional Fees, and Where Applicable, Protest Fee for International Application No. PCT/EP2017/025374, mailed Jun. 7, 2018.
International Search Report for International Application No. PCT/EP2017/025374, dated Jan. 9, 2019.
Written Opinion for International Application No. PCT/EP2017/025374, dated Jan. 9, 2019.
International Preliminary Report on Patentability for International Application No. PCT/EP2017/025374, dated Jul. 11, 2019.

* cited by examiner

METHOD FOR DETERMINING THE OCCURRENCE OF A VASCULAR COLLAPSE OF A BLOOD VESSEL IN OR AT THE EYE AS WELL AS A HOLDING DEVICE AND AN OPHTHALMODYNAMOMETRY ASSEMBLY

CROSS REFERENCE TO RELATED APPLICATIONS

This application is a national stage application under 35 U.S.C. 371 of PCT Application No. PCT/EP2017/025374 having an international filing date of 29 Dec. 2017, which designated the United States, which PCT application claimed the benefit of German Application No. 10 2016 015 577.9, filed 30 Dec. 2016, German Application No. 10 2017 001 677.1, filed 22 Feb. 2017, and German Application No. 10 2017 123 241.9, filed 6 Oct. 2017, each of which are incorporated herein by reference in their entirety.

The invention relates to a method for determining the occurrence of a vascular collapse of a blood vessel in or at the eye, especially at the entrance to the eyeball and/or at the exit from the eyeball, wherein pressure is exerted on the eye until a vascular collapse is achieved. The invention further relates to a holding device for use in ophthalmodynamometry and/or in a method of the aforementioned kind, as well as an ophthalmodynamometry assembly for determining the occurrence of a vascular collapse of a blood vessel in or at the eye.

In a customary method for determining the vascular pressure in blood vessels in or at the eye, the ophthalmologist places a contact lens on the eye and observes the blood vessels in the fundus through the contact lens. Then, by means of the contact lens, increasing pressure is exerted on the eye until a first vascular collapse occurs in the arterial vessel being observed. From the pressure exerted at this moment, the doctor can ascertain a diastolic arterial blood pressure value. If the pressure on the eye is further increased, at a certain pressure a total vascular collapse will occur. This moment marks the attainment of the systolic arterial blood pressure in the vessel under examination. The same procedure is used to determine the internal vascular pressure of the veins. In this case, however, there is no diastolic or systolic pressure, since the venous system is a low-pressure one. The pressure at which vein collapse begins is determined for the veins. A determination can also be made that a spontaneous venous collapse is already present at the existing intraocular pressure. From the venous pressure, the intracranial pressure can be determined.

The contact lens method for determining pressure or the occurrence of a vascular collapse in or at the eye has a number of drawbacks. First of all, the placement of a contact lens is often unpleasant to the person or animal being examined and may result in pain or irritation in the eye region. Moreover, the fact that different doctors will use different methods for placing and managing the contact lens is a source of error, as is the varying ability of doctors to reliably recognize the occurrence of a vascular collapse in the fundus region. Furthermore, there is the problem that the exertion of pressure with the contact lens presses the eyeball into the eye socket, or so-called orbita, with the result that the orbital venous pressure may be significantly increased by the measurement itself and the measurement as such may be falsified.

In order to improve reproducibility, the measurement can be at least partly automated. In this case, the determination of the occurrence of the vascular collapse is done not by observation by the doctor, but by imaging of the fundus or the vessels located there by use of a camera.

However, just as with the direct observation of the fundus by the doctor, the problem exists here that the angle of observation is relatively unfavorable on account of the position of the respective vessels, since the viewing may sometimes occur almost axially with respect to the vessel in the region of the entrance site of the optic nerve into the eyeball, the so-called papilla. Even for an experienced ophthalmologist, therefore, reliable determination of the vascular collapse in this region may be difficult. The position of the vessels at the eyeball represents a correspondingly greater hurdle for an automated recognition of a vascular collapse with the aid of recorded imaging data.

Against this background, the problem which the present invention proposes to solve is to provide a possibility for a more reliable and especially an automatable determination of the occurrence of a vascular collapse in the eye.

The abovementioned problem is solved according to the invention by a method with the features of claim 1, by a holding device according to claim 9 and by an ophthalmodynamometry assembly according to claim 29. Advantageous modifications are the subject matter of the dependent claims.

In the method according to the invention, the vascular collapse in the eye is not determined solely visually, that is, through external observation of the vessel by the doctor or by means of a camera or a similar imaging device, but rather from a measured temporal change in the blood flow, especially the mean flow rate of the blood in the blood vessel at issue. Corresponding experiments by the inventor have yielded the surprising discovery that the blood flow in the vessel at issue is suspended in a characteristic manner upon occurrence of a vascular collapse. Therefore, the occurrence of a vascular collapse in a vessel of the eye can be reliably detected by a time-resolved measurement of the blood flow and a determination made possible in this way of a temporal change in blood flow in the form of a temporary suspension.

The determination of the occurrence of a vascular collapse based on the temporal change in blood flow has the advantage over visual methods that a reliable inference of the presence of a vascular collapse is possible even with an axially limited view of the collapsing vessel. Depending on the method used for the determination of the blood flow or its temporal change, it is even advantageous to perform the measurement not in the axial direction of the vessel, but instead at the margin of the optic nerve, where the vessels run horizontally to the diagnostic beam. The measurement can be done in or against the flow direction of the blood inside the vessel. Finally, this is especially advantageous for measurement methods based on a phase shift of a backscattered signal relative to an incident signal, as shall be further discussed below.

Preferably, the blood flow is measured by means of an optical method, with the method of optical coherence tomography (OCT) being especially preferable. In particular, so-called Doppler OCT, i.e., optical coherence tomography using duplex technology, is a preferred method for determining the velocity of investigated objects.

In the OCT method, based on the fundamental principle of an interferometer, a measuring light beam is placed in relation to a reference light beam so that information can be gained from the interference of the two beams as to the structures investigated with the measuring light beam. In OCT, light sources with relatively short coherence length are commonly used. A suitable choice of light source spectrum enables the luminous radiation to penetrate to a certain depth in tissue structures, thus enabling provision of depth information as to the tissue being studied. OCT has the advantage that the lateral and the longitudinal resolution are decoupled from each other, since the lateral resolution is dependent on the numerical aperture of the imaging optics while the longitudinal resolution is primarily dependent on the spectrum or the spectral width of the light of the light source.

Accordingly, the OCT method enables creation of tomographically detailed three-dimensional images of tissue structures. For this reason, the method of OCT on the eye has already been used for some time in angiography, or so-called angio-OCT, for the representation of existing vascular structures.

As has now been surprisingly discovered, an OCT measurement can also be used on the one hand to represent the blood flow in the interior of vessels, and on the other hand time-resolved OCT can be used to detect changes in this blood flow with high precision as well. A suspension of the blood flow, such as occurs when a vascular collapse is present, can thus be detected with high precision by the OCT method. Thus, the occurrence of a vascular collapse in the eye can be determined in a dependable and non-invasive manner.

Of course, as an alternative or in addition to the basically preferred method of optical coherence tomography, other flow measurement methods are also suitable and can be used according to the invention. These include in particular the methods of scanning laser Doppler flowmetry (SLDF) and laser speckle flowmetry.

According to the invention, in a method for determining the occurrence of a vascular collapse in an arterial vessel in or at the eye, pressure is exerted on the eye until vascular collapse is achieved, and the vascular collapse is determined from a measured temporal change in blood flow in the blood vessel. Unlike the central artery, the venous system is a low-pressure system. In most instances, one may expect the collapse behavior of the central vein to be similar to that of the central artery. The same conditions for vascular collapse are present here as for the central artery. In this case as well, vascular collapse is determined from a measured temporal change in blood flow in the blood vessel. Since the venous pressure is dependent on intracranial pressure, venous pressure may also be used to measure intracranial pressure. The method according to the invention enables a determination of spontaneous venous collapse to ascertain a non-increased intracranial pressure, even without a dynamometric method. Only in those cases where no spontaneous venous collapse is present is it necessary to exert pressure on the eye until venous collapse is achieved. As a result, it may be provided according to the invention to exert pressure on the eye for the purpose of achieving an arterial vascular collapse or a non-spontaneous venous collapse until such time as the vascular collapse occurs. In cases where a spontaneous venous collapse is present, on the other hand, it is not necessary to exert pressure on the eye. The determination of a spontaneous vascular collapse in the venous system is also considered to be a dynamometric determination, because the spontaneous intraocular pressure here is sufficient to generate a spontaneous venous collapse.

Compression site radial to the eyeball equator: In order to cause vascular collapse in the arterial vessel under observation, the pressure on the eyeball is preferably exerted from the side or the sideways direction, that is, at least substantially transversely to the viewing axis of an eye to be examined. For one thing, the observation path for an optical blood flow determination is free in this way. For another, a falsification due to pressing the eyeball into the eye socket and the consequent compression of the eye socket or due to an increase in tissue pressure in the eye socket is significantly reduced.

Eyelids as the compression site: The pressure exerted on the eye is especially preferably indirect, that is, not directly on the eyeball. If the pressure is exerted on the eyeball across the upper and/or the lower eyelid of the eye, the systematic error due to the pressure exerted during a vascular pressure determination is further minimized, since the lid possesses a buffering effect in the low pressure range, which represents a significant advantage when connecting the pressure head of the dynamometer. By contrast, connecting directly to the eyeball represents an uncontrolled primary pressure increase, a problem affecting all other methods which exert pressure directly on the eyeball including contact lens dynamometry. An especially suitable site for applying the necessary pressure is in the region of the temporal angle of the eyelid, because the pressure application here occurs radially to the eyeball equator.

The pressure exerted on the eye may be set manually and/or automatically, wherein an automatic setting of the pressure is done in particular by a measurement and evaluation device. The pressure actually exerted on the eye can moreover be measured by a sensor or determined otherwise, especially by the measurement and evaluation device. Alternatively or additionally, furthermore, a visualization of the applied pressure may be performed. This can be done through a mechanical scale or a digital display, for example.

Especially for the control and/or readout of measurement data, such as a pressure exerted on the eye, a data transmission may occur between the pressure generator, a sensor and/or the measurement and evaluation device or a measurement assembly in general. The transmitted data accordingly encompasses preferably control data and/or measurement data, especially a pressure value. The measurement assembly is preferably an optical coherence tomography assembly and/or a scanning laser Doppler flowmetry assembly and/or a laser speckle flowmetry assembly. Thanks to a direct data transmission between a device for control and/or evaluation and the pressure generator or sensor, an automation of the method is ultimately possible. The data transmission preferably occurs in bidirectional manner.

The data transmission between the pressure generator, the sensor and/or the measurement and evaluation device or the measurement assembly preferably occurs wirelessly. In this way, a device designed for the method according to the invention permits a significant reduction in expense with respect to connection and operation. A wireless connection moreover enables a monitoring and control of the method without excessively burdening the freedom of movement of a person performing the examination. The data transmission occurs in particular over widely used protocols, such as Bluetooth and/or wireless LAN. Besides low costs for the corresponding modules, this ensures a good compatibility of various hardware components working together in the context of the method according to the invention.

A preferred embodiment of the method according to the invention, moreover, provides a remote control or readout of the pressure generator, the sensor and/or the measurement and evaluation device, especially via a remote data transmission line such as the Internet. For one thing, this allows medical staff to carry out or control the method without being physically present at the site of use. For another, a technical diagnosis and/or a setting of parameters, such as the entering of updates, can be performed by technical service personnel remotely by means of a remote data transmission.

From the occurrence of a vascular collapse in a vessel of the eye as reliably determined by the method according to the invention, in one preferred embodiment of the method according to the invention it is then possible to determine the vascular pressure of the vessel under observation. This uses as its basis the measured pressure exerted on the eye at the moment of occurrence of the vascular collapse. In similar manner, possibly by an appropriate calibration, the intracranial pressure may also be inferred through the vascular pressure from the pressure exerted upon occurrence of the vascular collapse. For this, the determination of the venous blood pressure at the eye is of particular importance. However, a reliable determination of a venous vascular collapse at the eye is especially problematic with known visual methods. Furthermore, the venous vascular pressure is especially prone to disruptive influences on the measurement due to a change in the tissue pressure caused by the measurement. This is where the invention comes in, with the advantages of a determination of the vascular collapse based on the blood flow or a change in the blood flow taking effect.

The detection of the pressure exerted on the eye is done in a manner preferably decoupled from the generation of the pressure, for example by means of a pressure generator. This also enables a measurement during a change, especially a rise, in pressure. Otherwise, the detected pressure would always be influenced by the continual or stepwise change in pressure in the system, which would make the measurement data unreliable or unusable.

In the case of the measuring of the venous blood pressure, the vascular collapse occurs only once in the case of a monophase venous collapse. Such a one-time event is generally hard to detect clearly, and thus reliably. In this regard, an undulating exertion of pressure results in a repeat occurrence of the vascular collapse. The detectability of the vascular collapse is distinctly increased in this way. For this purpose, an appropriately modulated actuation of a pressure generator is provided, so that an undulating exertion of pressure can be performed in automated manner. A target mean value can be specified, around which the exerted pressure fluctuates with a preferably adjustable amplitude. The pressure range in which a fluctuation occurs is preferably between the pressure level triggering a collapse and 3 mmHg, preferably 5 mmHg, below that.

A further aspect of the invention for solving the above-indicated problem is a holding device, especially one designed for use in ophthalmodynamometry or in a method of the above-described kind. The holding device according to the invention comprises a pressure generator or dynamometer for exerting an external pressure on the eye as well as a holding element for holding and/or positioning the pressure generator relative to the eye. Together with the pressure generator, the holding device according to the invention realizes in particular the function of a dynamometry assembly.

The holding device according to the invention can also be used advantageously for determining the aqueous humor outflow resistance in oculopressure tonometry (OPT).

The holding device according to the invention or dynamometry assembly makes possible in particular an examination of the eye with respect to aqueous humor dynamics in the context of a glaucoma diagnosis. In this case, the aqueous humor outflow resistance can be determined by a change in the internal pressure of the eye. For this, the dynamometry assembly can be coupled to an air tonometer and a measurement and evaluation device, for example.

Now, to determine the outflow resistance, the intraocular pressure can first be determined with the air tonometer, for example. After this, an application of pressure to the eye is performed by means of the pressure generator of the dynamometer. After suspending the application of pressure to the eye, a further measurement is taken of the intraocular pressure. The value measured afterwards is generally lower, since aqueous humor has been drained on account of the external pressure. The outflow resistance of the eye to the aqueous humor can be inferred from the difference between the two pressure values found. The lower the intraocular pressure after the pressure loading, the lower the outflow resistance, i.e., the more aqueous humor has drained out.

Thus, unlike classical dynamography, a determination of the intraocular pressure is done before and after the dynamometric pressure loading, instead of a determination of the decrease in the intraocular pressure at the moment of the dynamometric pressure loading. Since more aqueous humor has drained out during the intraocular pressure increase, the intraocular pressure after the pressure loading is accordingly greatly decreased. This makes it easier to differentiate between a disturbed and a normal drainage with regard to facility.

Even though the above-described method of oculopressure tonometry (OPT) has basically been known for a long time, its high methodological expense has thus far prevented its widespread adoption. The present invention offers a substantial methodological simplification and even the possibility of largely automating the OPT measurement procedure. In this way, important information about the outflow resistance can be obtained in future at low expense and with relatively short examination times. This has advantages in regard to a possible use in the context of therapy monitoring, for example.

An examination assembly for oculopressure tonometry (OPT) preferably comprises a dynamometry assembly with the holding device according to the invention and a measurement instrument for determining the intraocular pressure, especially an air tonometer, as well as an evaluation device. With such an assembly, a disturbed drainage of the aqueous humor can be diagnosed at low expense and preferably in an automated manner.

The invention furthermore involves a method for OPT making use of the holding device according to the invention and the use of the holding device according to the invention for oculopressure tonometry.

Moreover, blood pressures of the retinal arteries and veins as well as intracranial pressure can be determined. For this, the dynamometry assembly can be coupled to an appropriate measurement instrument, preferably an optical coherence tomograph. The measurement instrument in this case serves as a collapse detector. A subsequent evaluation and/or output of the measurement data by means of an evaluation or data processing device provides insight into the prevailing vascular pressures in and at the eye.

Furthermore, by connecting an OCT instrument and the dynamometry assembly from the holding device according to the invention to a pressure generator, it is possible to determine, through papillary microcirculation, the degree to which the optic nerves can tolerate a dynamometric loading. During glaucoma, a relationship is suspected between the occurrence of damage to the optic nerves and disturbed papillary microcirculation. In this connection, the invention can help provide valuable clues about any possibly damaging.

As a fourth field of use, we have electro-physiological diagnosis of the eye. A connection of the dynamometry making use of the holding device according to the invention to the measurement of visually evoked potentials (VEP)

and/or the method of electroretinography (ERG) makes possible an electro-physiological retina or optic nerve diagnosis in accordance with the applied pressure. This may provide insight into the sensitivity of the optic nerves to changes in pressure conditions and/or a determination of retinal activity and its change when intraocular pressure is increased.

The pressure generator is connected to the holding element in such a way that, when the holding device is used as intended, pressure can be exerted on the eye from the sideways direction. The exertion of pressure is done preferably across the upper eyelid and/or the lower eyelid, especially in the area of the temporal angle of the eyelid. In this way, on the one hand, the direct contact of a portion of the pressure generator with the eyeball is avoided, which is often perceived to be unpleasant by the person being examined. On the other hand, thanks to this kind of indirect exertion of pressure, the effect of a slight pressure increase by connection of the dynamometer head in the interior of the eye is avoided on account of the positioning of the pressure probe itself, or at least reduced, which might otherwise lead to a wrong measurement.

In particular, the holding device is designed for self-supported attachment to the head of the patient. The holding device can preferably be secured to the head of the patient and/or be connected to the head of the patient in such a way that the holding device is held solely via the head of the patient for the exertion of pressure on the eye. In particular, the holding device according to the invention differs from stationary holding devices that have a frame design and are connected to a base, such as a treatment table or the like, and that are used in the prior art particularly for the mounting of optical devices during eye examinations.

Further, the holding device is designed in particular such that, when being worn, or when the holding device is held on or attached to the head of the patient, the holding element with the pressure generator is arranged on one side of the head, i.e., at the side of the head, for the exertion of pressure on the eye, while a further holding element of the holding device lies against the head on the other side of the head, so that an abutment is created for the exertion of pressure on the eye.

For the pressure determination, the dynamometry assembly, especially the holding device and/or the pressure generator, preferably comprises a pressure determination device having a pressure sensor. The pressure determination device is preferably decoupled from the pressure generation at the pressure generator. In this case, therefore, the exertion of pressure occurs independently of a pressure measurement unit or a pressure sensor. This prevents an influencing of the measurement by the pressure change in the pressure generator. A measurement of the pressure is thus also possible during a continuous or stepwise pressure change.

In an especially preferred embodiment, the holding device according to the invention is designed to be portable or self-supporting. This means that during use, i.e., when the pressure generator is situated in the intended position relative to the eye for its use, the holding device can be placed on a person or animal and be supported by them. In this case, a supporting mechanical connection between the holding device and a stationary or fixed item not connected to the patient, such as a treatment table or the like, is not provided.

In an especially suitable embodiment, the holding device is designed for this in the form of an eyeglass frame. In this way, a person can comfortably put on the holding device to perform an ophthalmodynamometric procedure, with the pressure generator having already been placed in a measurement-correct position for a measurement or an exertion of pressure with no major adjustment effort. Furthermore, due to the automatically correct positioning of the pressure generator relative to the eye when using the holding device, the performance of the ophthalmodynamometric measurement need not necessarily be done by the doctor, but instead can be delegated by the doctor to medical staff. Eyeglasses have a defined relationship to the anatomy of a person. It takes into account the basic width of the head as well as the pupil distance, i.e., the spacing between the eyes. Thus, with an eyeglass frame as the holding device, there is a fixed relationship to the anatomy of the face, especially the eyeball.

The holding element of the holding device is accordingly preferably designed as an arm of an eyeglass frame. The holding device in this case may be placed like glasses on the head, so that the holding element runs along the side of the head and the pressure generator is arranged in the eye region and to the side of it. Of course, the holding device is preferably symmetrically designed for a secure fit, i.e., it has two eyeglass arms, for example. The second arm of the eyeglass frame forms an abutment on the other side of the head of the patient, in order to assure a stable position of the pressure generator with respect to the eye during the exertion of pressure on the eye. Furthermore, it is not necessary for the holding device to have an actual viewing window or even eyeglass lenses. Ultimately, the head-encircling form of an eyeglass frame is the important aspect, making such a form especially suitable for the holding device according to the invention.

In an alternative embodiment, the holding device according to the invention may be designed as a helmet and/or have a fixing band for fastening to the head of the wearer of the holding device. The outer shape of the holding device and the nature of the fastening and positioning of the pressure generator relative to the head or eye of the wearer can be chosen in accordance with the particular application situation. In particular, requirements on the firmness of seating of the holding device, the wearing comfort, the wearing duration and possibly the accessibility of the eye to further examination instruments should be taken into account.

If a suitable support frame is already present, for example in the form of eyeglasses regularly worn by the person, the holding device and especially the holding element may also be designed to be connected to an eyeglass arm. The eyeglasses worn by the person are generally already optimally adapted to the shape of his or her head, so that a secure seating and good wearing comfort are assured. The holding device or the holding element according to the invention with the interconnected pressure generator may in this case be secured for example to the eyeglass arm to the side of the eye region or to another suitable part of the eyeglass frame. A secure yet relatively easily removable connection is preferred here, for example by means of a holding clip or by a screw connection.

During use, the pressure generator exerts pressure on the eye preferably across an appropriate contact element for placement against the eye or against portions of the eye. The contact element is designed in particular for placement against the upper eyelid and/or the lower eyelid, preferably in the region of the temporal angle of the eyelid. Thanks to the lid dynamometry, there is no need for a surface anesthesia of the eye. This has the advantage, for one thing, that the procedure is much more pleasant for the person being examined. For another, the examination may be delegated by the doctor to assisting staff when no anesthesia is used.

Especially suitable is a design of the contact element as a knob, a plunger, and/or a contact plate. The specific form of the contact element will ultimately depend on the particular application. The contact element may for example have a different design according to whether pressure is to be exerted on the upper eyelid, the lower eyelid, or both eyelids.

The contact element of the pressure generator is preferably mechanically, hydraulically and/or pneumatically movable. Especially in the case of a pneumatically movable contact element, the pressure generator preferably has a piston/cylinder unit for the movement of the contact element.

An improved placement of the contact element against the respective contact area on the eye is achieved when the contact element is hinge-mounted. For a hinged mounting of the contact element, this may be hinged in particular to the piston rod of a pneumatic cylinder or a piston/cylinder unit of the aforementioned kind in such a way that the contact element can swivel in one or more directions.

Especially for the simultaneous exertion of pressure on the upper and the lower eyelids, the contact element may comprise a plurality of separate contact sections, preferably two contact sections, which in turn are intended for placement against the eye or against portions of the eye, that is, in particular the upper eyelid and/or the lower eyelid of the eye. The contact sections may alternatively or additionally to a hinged mounting of the contact element also be individually hinged and/or swivel-mounted, in order to assure an optimal placement against the corresponding contact region of the eye. This design of the dynamometer as a double-head dynamometer entails the advantage that the force exerted on the eyeball is centered. Shear forces which may occur in the case of inexperienced users and especially in connection with traditional dynamometers are in this way reduced to a minimum.

The lateral extension or diameter of a contact section of the pressure generator is preferably between 2 mm and 10 mm, preferably between 4 mm and 8 mm, especially preferably between 6 mm and 7 mm. In particular, it is not necessary for a contact section to have the same extension in both lateral dimensions. Instead, according to the invention, an oblong, especially an elongated oval, shape of the contact section may be provided.

The contact element and/or at least one contact section has a curved and/or arched surface in one preferred embodiment. The curvature or arching is convex in particular, i.e., projecting at the center in the direction of the exertion of pressure by the pressure generator. It is not necessary for the contact element or The radius of curvature in particular is slightly larger than the usual radius of curvature of the eyeball and preferably amounts to between 5 mm and 15 mm, preferably between 7 mm and 13 mm, especially preferably between 9 mm and 11 mm.

Alternatively or additionally, the contact element and/or one or more contact sections may also be adjustable to the angle. Of course, the angles of the contact sections need not be identical with respect to the movement direction and/or to each other. For example, there may be a slight angling of one contact section with respect to the other. In this way, the dynamometer can be individually adapted in an optimal manner to the particular eye contour.

The contact element is preferably designed such that, when brought up to the eyeball, a uniform placement against both eyelid ends occurs, so that no strong pressures are produced on the top or bottom end. Preferably, the dynamometer head, i.e., especially the contact element of the pressure generator, is oriented substantially perpendicular in the noncontact state.

From a hygienic perspective, it is advantageous for the contact element and/or the contact sections to be interchangeable. By a simple replacement of one used part by a new and especially a sterile part, there is no need for an elaborate cleaning and sterilizing of the elements coming into immediate contact with body parts between measurements on different people. Alternatively or additionally, an interchangeable cover may be provided for the contact element and/or the contact sections, with a new one being put on prior to the use of the holding device.

For the protection of the eye or for special application situations, for example during measurements in a particular pressure range, the pressure exerted by the pressure generator may be limited to a particular maximum value. For this, the pressure generator is preferably designed so that upon reaching a set and/or settable maximum pressure on the eye, there is automatically no further exertion of pressure by the pressure generator. This may basically be done by limiting the path of movement of the contact element moved by the pressure generator, for example by means of a mechanical end stop. Furthermore, solutions are also possible according to the invention which are based on a measuring of the pressure exerted and an automatic shutoff and/or reversal of the pressure generator upon reaching the set and/or settable maximum pressure.

In order to conform to specific anatomical circumstances of the user of the holding device according to the invention, in a preferred embodiment it may have an adjusting device. By means of the adjusting device, in particular the width of the holding device can be adapted to the head size of the wearer. This is of most significant advantage with regard to the proper fit of the holding device and the positioning of the pressure generator relative to the eye when the holding device is configured as an eyeglass frame. Moreover, the wearing comfort is increased by such an adjustment option for the wearer of the holding device, so that a use free of complaint is possible even over lengthy periods of time, for example for long-term collection of ophthalmological data.

The adjusting device may be designed, especially in the case of an eyeglass frame-type holding device, as an adjustable bow, especially one that is displaceable and can be fixed in different positions, preferably on the frame. In the worn state or state of use of the holding device, the adjusting device is preferably situated in the eyebrow region of the wearer. This allows easy access to the adjusting device and a problem-free setting of an optimal width of the holding device.

The adjusting device may be designed in various ways, depending on the application situation. Preferred embodiments include a design as a push-in sleeve, adjusting bow, sliding rail system and/or screw-thread system, each optionally in connection with click stops and/or a fixing means, such as a quick release clamp or a fixing screw.

In the context of the invention, a multi-piece adjusting device or multiple adjusting devices may also be provided, each preferably allocated to the holding elements. If the holding device is designed as an eyeglass frame, the adjusting devices may be arranged for example on the frame with each allocated to one side, i.e., to an eyeglass arm.

The adjusting device may alternatively or additionally also be designed as an individual adjusting device, preferably centrally situated. In this way, an adjusting of the shape or size of the holding device can easily be performed with a single adjustment at a central location.

Furthermore, an electromotorized, pneumatic and/or hydraulic adjustment of the holding device is also possible with the adjusting device. In this case the adjustment may furthermore be done by means of a remote control and/or automatically.

If a pressure of a particular force is exerted by means of the pressure generator on an eye, this same force also acts in opposite direction on the pressure generator and through it on the holding element or the holding device. For this reason, a sufficiently sturdy abutment is required, so that an undesirable shifting or twisting of the holding device is prevented and the pressure can be exerted on the eye in a well-defined form. When the pressure is slight, the forces which occur may still be small enough so that the holding device itself—depending on its form, the type of material, and thickness of material—is sufficiently rigid and firmly seated to resist the counterforce of the pressure generator. As the pressure increases, however, the holding device, especially if it is designed as an eyeglass frame, will yield to the counterforce and move according to the existing degrees of freedom or change its shape. For this reason, in a preferred embodiment of the holding device according to the invention, a defined abutment is created, by which the countering force is absorbed and the holding device has a corresponding degree of freedom removed from it, which would otherwise allow an unwanted movement and/or deformation.

Such an abutment may be constituted in a defined manner by one or more abutment elements arranged on the contralateral side with respect to the pressure generator at issue. An abutment element may for example be designed to project from a base body of the holding device and/or a holding element, such as in the form of a pin or a knob. According to the invention, however, a bulge, a local reinforcement, or a point distinguished by the shape of the holding device and/or a holding element, especially a projecting point, may serve as the abutment element.

An abutment element may be removable or interchangeable. In this way, different abutment elements can be arranged on the holding device, which are ultimately adapted in their shape, size and/or number to the anatomy of the wearer of the holding device. Moreover, a multitude of receiving options for an abutment element may be provided at different positions of the holding device and/or an abutment element may also be arranged in movable manner on the holding device such that the position of the abutment element can be adapted to the head shape of the wearer. Furthermore, the contact abutment itself may be adjustable in size, so that for example an adjusting thread may bring about a bearing of the abutment element and thus of the holding device as such against a definite contact point on the head of the wearer when worn. The position change and/or the size change of an abutment element may furthermore also be brought about by electric motor and/or be remote controlled and/or automated.

Ideally, the bracing of the holding device occurs against a sufficiently firm location. In this regard, the cranial bone will be considered first and foremost. It has been found that an optimal force cushioning is made possible by a bracing of the holding device against the bony margin of the eye socket (orbita) on the side of the head opposite the eye subjected to the pressure. In this way, a suitable abutment is created to make possible the exertion of pressure on the respective eye at the optimal angle of around 90° on the equator of the eyeball, preferably at the temporal angle of the eyelid across the upper eyelid and/or the lower eyelid. In this way, even when the pressure exerted is great, an exact and stable positioning of the holding device and thus of the pressure generator is made possible.

An alternative or additional option for bracing the holding device against the counterforce of the pressure generator may be realized by a symmetrical exertion of force from two opposite sides. The holding device in this case preferably carries at least two pressure generators, which when worn are arranged on opposite sides of the head. During the exertion of pressure on an eye by a first pressure generator, an oppositely situated second pressure generator works synchronously in the opposite direction. The orientation of the second pressure generator is preferably such that its head, i.e., its contact element (optionally with one or more contact sections) presses against the bone of the eye socket rim and thus cancels the force of the first pressure generator on the eye in relation to the holding device, so that the desired position stability is achieved.

The mounting of multiple pressure generators on opposite sides furthermore enables a reconfiguring of the dynamometry assembly for a bilateral eye examination by means of slight adjustments, which furthermore can be automated.

The holding device in one preferred embodiment comprises a device which enables a precise positioning of the pressure generator especially in the worn state. A displacement device is preferably provided for the movement of the pressure generator in the distal direction and/or in the vertical direction. A displacement in the distal direction means in this context that the holding device when worn produces a movement in the viewing direction, i.e., along the side of the head between face and ear or occiput. "Vertical" on the other hand refers to the height adjustment of the position of the pressure generator. It is especially advantageous to have both movement options available, so that an exact orientation of the pressure generator relative to the eye can be achieved.

The displacement device is preferably electromotively, pneumatically and/or hydraulically driven and/or remote-controllable in particular.

By a means for determining the state of the displacement device, such as a position sensor, the absolute position of the pressure generator moved by the displacement device can be recorded or read out. This enables a regulating of the position of the pressure generator in the course of an automated dynamometry sequence. Furthermore, designated points, such as an optimal person-dependent position of the pressure generator relative to the eye, can be saved in memory and called up at a later time and approached, in particular.

Moreover, thanks to the possibility of moving the pressure generator in two dimensions relative to the head of a person, a positioning of the pressure generator on the bone of the eye socket rim can be performed. This pressure generator can be used at this location as a means of bracing the holding device in the sense of a dynamic abutment when pressure is being exerted on the eye by a pressure generator at the opposite side of the head.

The travel path of the pressure head of a pressure generator when exerting pressure on the eye is typically twofold and is composed of the travel path from the position of rest to the contact with the eye and an additional stroke of preferably between 1 mm and 6 mm, especially between 2 mm and 5 mm.

The pressure produced in the eye with the pressure generator preferably corresponds to a weight of 1 g to 20 g, especially up to 40 g, more preferably up to 60 g. In certain cases, however, the pressure may also be significantly higher and correspond for example to a weight of 150 g. The time of action is preferably between a few seconds and up to 5 min, but it may also be longer. The specific values are highly dependent on the particular application.

For different application scenarios, the following data may serve as guidelines, which are not to be seen in any way as being limiting to the scope of the invention.

For venous and intracranial pressure determination: pressure loading corresponding to 1 g to 20 g, time of action 10 s to 2 min; for arterial blood pressure measurement: pressure loading corresponding to 40 g to 140 g, time of action 1 min to 3 min; for determination of the outflow resistance by means of OPT for glaucoma diagnosis: pressure loading corresponding to 30 g to 50 g, time of action 1 min to 5 min; in the context of a pressure tolerance test using optical coherence tomography: pressure loading corresponding to 10 g to 30 g, time of action 2 min to 4 min; electrophysiological examinations: pressure loading corresponding to 10 g to 30 g, time of action 1 min to 5 min.

The movement speed of the dynamometer head is preferably between 0.5 mm/s and 10 mm/s, preferably between 1 mm/s and 5 mm/s.

The shutting off of the pressure increase or the ending of the measurement process occurs upon reaching a given pressure value and/or extension distance, especially automatically and/or manually, for example by an emitted signal.

In the case of measuring the venous blood pressure, one must note the particularity that the vascular collapse occurs only once in the case of a monophase venous collapse, and thus can only be detected unreliably. However, an undulating exertion of pressure results in a repeat occurrence of the vascular collapse. The detectability of the vascular collapse is distinctly increased in this way. For this purpose, the pressure generator is designed for an undulating exertion of pressure and/or a correspondingly modulated exertion of pressure is provided. An undulating exertion of pressure may also be automated in particular. A target mean value can be specified, around which the exerted pressure fluctuates with a preferably adjustable amplitude. The pressure range in which a fluctuation occurs is preferably between the pressure level triggering a collapse and 3 mmHg, preferably 5 mmHg, below that.

The holding device in one preferred embodiment comprises a means of data transmission in the form of a corresponding interface. The data transmission interface is preferably designed for the transmission of control data and/or measurement data, especially a pressure value. It is thus possible to control the pressure generator in its operation, and optionally a positioning device, from a distance, and/or to read out sensor data, such as a pressure value, without having to remove the holding device. Moreover, with the data transmission interface a real-time control and/or readout can occur during measurement. Thus, the data transmission interface creates a feedback possibility of the dynamometry assembly to a measurement assembly, especially an OCT instrument.

Especially for the control and/or readout of measurement data, such as a pressure exerted on the eye, a data transmission interface can establish a data transmission between the pressure generator, a sensor and/or the measurement and evaluation device or a measurement assembly in general. The transmitted data accordingly involves primarily control data and/or measurement data, especially a pressure value. The measurement assembly is preferably an optical coherence tomography assembly and/or a scanning laser Doppler flowmetry assembly and/or a laser speckle flowmetry assembly. Thanks to a direct data transmission between a control and/or evaluation device and the pressure generator or sensor, an automation of the method ultimately becomes possible.

The interface is preferably designed for bidirectional data transmission.

The data transmission between the pressure generator, the sensor and/or the measurement and evaluation device or the measurement assembly is preferably wireless. This significantly reduces the expense in regard to the connection and operation of the dynamometry assembly. A wireless data transmission interface furthermore makes possible a monitoring and control of the process without a person performing the examination being excessively limited in their freedom of movement. The data transmission interface in particular supports widely used protocols, such as Bluetooth, wireless LAN, and/or NFC. Besides low costs for corresponding modules, this ensures a good compatibility between different interacting hardware components.

Further, there is preferably provided an interface for the remote control or readout of the pressure generator, of the sensor, and/or of the measurement and evaluation device, especially via a remote data transmission line such as the Internet. For one thing, this allows medical staff to carry out or control the procedure without being physically present at the site of use. For another, a technical diagnosis and/or a setting of parameters, such as the recording of updates, can be performed by technical service personnel remotely by means of a remote data transmission.

Preferably, the dynamometry assembly is designed such that a transmission and/or output of data in relation to the current pressure exertion, the measurement program running (venous pressure measurement, arterial pressure measurement, OPT/glaucoma diagnosis, pressure tolerance determination on the optic nerve, etc.), a feedback of the dynamometry assembly to a measurement assembly, especially an OCT assembly, and/or the time between individual measurement steps, for example during the OPT for glaucoma diagnostics. Moreover, the transmitted data can be evaluated by means of an evaluation device in such a way that, for example, a value for the facility of drainage can be issued directly from the measured pressure difference before and after the loading during the OPT.

The possibilities for remote control and automation include in particular a control and/or a readout by a stationary computer, a tablet computer, a smartphone or the like, and it is also preferably possible via the Internet. Thus, settings can be made and measurements performed over large distances. Through the data transmission interface, medical staff and/or technical service personnel may gain access to the dynamometry assembly and/or measurement assembly.

The possibility of automating the optical dynamometry by the holding device or dynamometry assembly according to the invention makes it possible to do away with the otherwise-required local anesthesia of the eye. Such a local anesthesia usually destroys the separating film on the eye, making it difficult for the doctor and for optical measurement instruments to look through the pupil into the eye. Moreover, by eliminating a local numbing of the eye, the procedure becomes much more pleasant for the person and the performance of the examination becomes a task which may be delegated.

Moreover, a readjustment in event of a drop in the eye pressure, which is regularly observed in the case of lengthy exertion of pressure, becomes possible. The invention thus enables an easy and preferably automatic maintenance of constant pressure in the sense of a so-called "iso-tonography." The possibility of coupling the dynamometry assembly or the holding device with the pressure generator to a corresponding measurement assembly allows a feedback of the exerted pressure with the intraocular pressure change induced by this. Surprisingly, it has been discovered in corresponding experiments that an approximately linear relationship exists between these two quantities over a broad range.

The pressure to be applied by means of the pressure generator for a particular target intraocular pressure depends primarily on the anatomy of the eye being examined. In particular, the size of the eyeball and the ocular rigidity or thickness of the wall of the eyeball play a major role in its elasticity. Accordingly, the same exerted pressure does not always lead to a vascular collapse. A calibration of the system is done preferably by means of a contact tonometer via the cornea. Thanks to the sideways exertion of pressure on the eye made possible by the holding device according to the invention, the measurement of the intraocular pressure via the cornea is not affected. The aforementioned individual anatomically related differences are less important in the low-pressure range. In the higher-pressure range, however, a correction is warranted at regular intervals of time, such as every 30 s or every minute, for example by means of a pressurized air-based non-contact tonometer (NCT).

The invention moreover relates to an ophthalmodynamometry assembly for determining the occurrence of a vascular collapse of a blood vessel in or at the eye. By means of the ophthalmodynamometry assembly according to the invention it is possible to determine the vascular collapse especially in the area of the entrance of the vessel to the eyeball and/or at the exit from the eyeball.

The ophthalmodynamometry assembly in the most simple embodiment comprises a pressure generator for exerting a pressure on the eye and a measurement and evaluation device for determining the occurrence of a vascular collapse in the eye.

According to the invention, the pressure generator of the ophthalmodynamometry assembly is held by a holding device in the above-described manner or is connected to a holding device of the above-described kind. A further aspect of the ophthalmodynamometry assembly according to the invention, which can be realized alternatively or in addition to the connecting of the pressure generator to a holding device in the above-described manner, is that the measurement and evaluation device is designed for an indirect determination of the vascular collapse from the ascertained change in blood flow of a blood vessel at the entrance to the eyeball and/or at the exit from the eyeball.

The benefits of a pressure generator held by a holding device in the above-described manner have already been discussed. Of course, as needed, the measurement and evaluation device of the ophthalmodynamometry assembly or parts thereof may be held by the holding device or be connected to the holding device. The same applies in particular to a pressure determination device optionally realized separately from the pressure generator.

A pressure determination device by means of which the pressure exerted on the eye can be measured, displayed, and/or determined in particular in other indirect ways can basically also be provided, physically separated from the pressure generator and in particular not connected to the holding device.

In an especially preferred embodiment of the ophthalmodynamometry assembly according to the invention, the measurement and evaluation device is designed to determine the change in the blood flow by means of an optical method, the layout being preferably suitable for the method of time-resolved optical coherence tomography in particular. A vascular collapse on a blood vessel of the eye, especially at the entrance or exit point of the vessels near the entrance point of the optic nerve in the eye, i.e., at the papilla margin or in the papillae funnel, can be reliably determined in this case, even with restricted visual access or an axial vascular collapse which is otherwise difficult to detect.

In order to carry out the method of optical coherence tomography, the measurement and evaluation device comprises in particular a light source with relatively short coherence length and with a suitable spectrum for the penetration of the tissue being examined. The light of the light source for an OCT measurement is, for one thing, deflected by a beam splitter through the pupil of the eye onto the retina, and also taken to a reflector, such as an ordinary mirror.

The light reflected back by this reflector and the light backscattered from the area of the fundus again passes through the beam splitter and optionally arrives via a corresponding imaging optics at a detection device. The detection device is preferably designed to register a two-dimensional image, for example as a camera or an optical sensor array. The incident beams, that is, the measuring beam of the light backscattered from the eye and the reference light beam reflected back from the reflector, now interfere with each other in accordance with the structure of the fundus thus illuminated.

The detection device accordingly registers in particular a two-dimensional distribution of interference information of the two beams. From this, it is possible to draw conclusions about the tissue structures in the observed fundus and furthermore to obtain information in particular about the movement of the blood in the observed vessels, that is, about the blood flow. Thus, from repeat measurement at short intervals of time one gets a time-resolved representation of the particular tissue and the blood flow in the vessels there. In the method according to the invention, it is advantageous that a quantitative or absolute blood flow measurement is basically unnecessary, since a qualitative detection of a characteristic change, i.e., the suspension of the blood flow, is ultimately enough to detect the presence of a vascular collapse.

The measurement and evaluation device comprises an evaluation unit for the automatic determination of a suspension of the blood flow and thus the presence of a vascular collapse, by means of which the information garnered with the detection device can be evaluated manually, partly automatically, or fully automatically. The evaluation of the data by the evaluation unit may also be done by software, in particular. The necessary measurement windows in the context of the optical detection are optionally positioned manually or automatically, or their automatic positioning is checked on the measurement image.

The ophthalmodynamometry assembly preferably comprises a control device for the automatic or at least partly automated performance of an ophthalmodynamometric measurement or an ophthalmodynamometric method and/or a method of the kind described above. For this, the control device is coupled in particular to the pressure generator and the detection device as well as the evaluation unit. Moreover, a back channel from a pressure determination device to the control device can be provided, in order to regulate the pressure exerted to a particular value. In particular, measurement even during rising dynamometric pressure is provided, which would be harder to accomplish in pneumatic methods.

For the automated performance of a determination of the occurrence of a vascular collapse at the eye, the appropriately designed control device can now cause the pressure generator to exert an increasing pressure on the eye, while the light source, optionally also actuated by the control device, illuminates the eye and the optical layout of the ophthalmodynamometry assembly.

Now, at short intervals, the detection device performs an ongoing recording of the interference pattern resulting from the structure of the tissue in the fundus, which is monitored by the evaluation unit for the presence of a suspension of blood flow in the vessels.

If a vascular collapse is detected by a suspended blood flow, either because the evaluation unit arrives at such a conclusion or the user determines the vascular collapse by a visualization of the data recorded by the detection device, the pressure exerted on the eye at this moment can be read out by the pressure determination device, noted down, and/or stored in memory. Moreover, instead of or in addition to the exerted pressure, the evaluation unit can be made to store the image information or the recorded detection device data along with other parameters such as the power of the light source and/or the time information for the recording.

The invention shall now be explained more closely with the aid of exemplary embodiments. All of the features described and/or depicted form the subject matter of the present invention in themselves or in any given combination, regardless of their summarization in the claims or references back to them.

Figure 2:
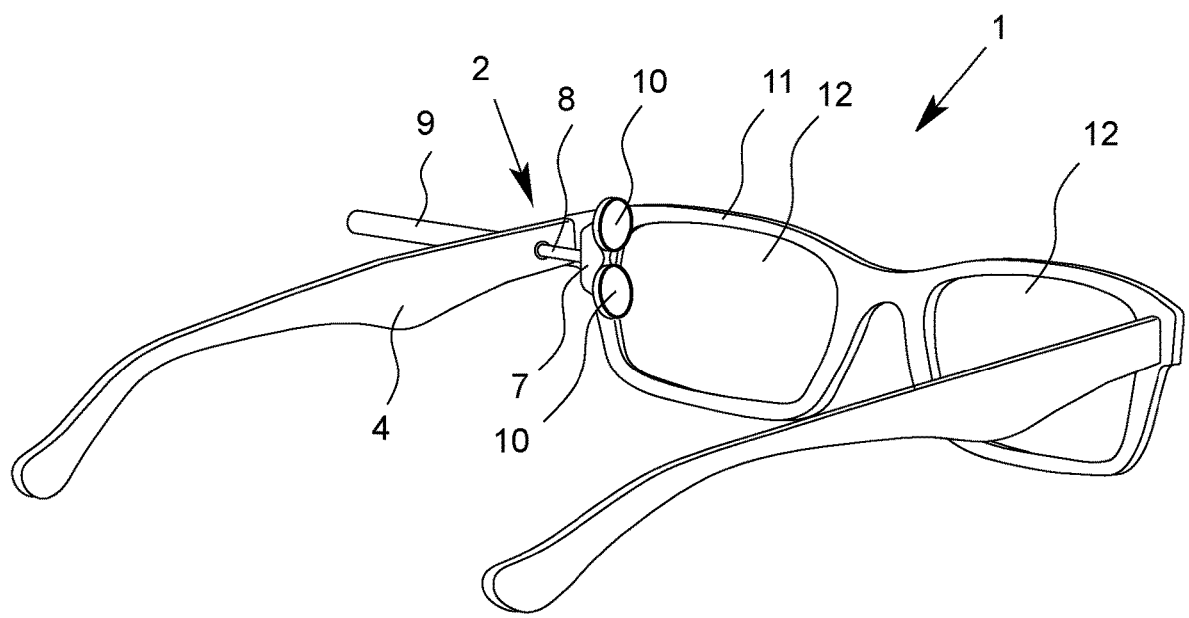
Figure 3:
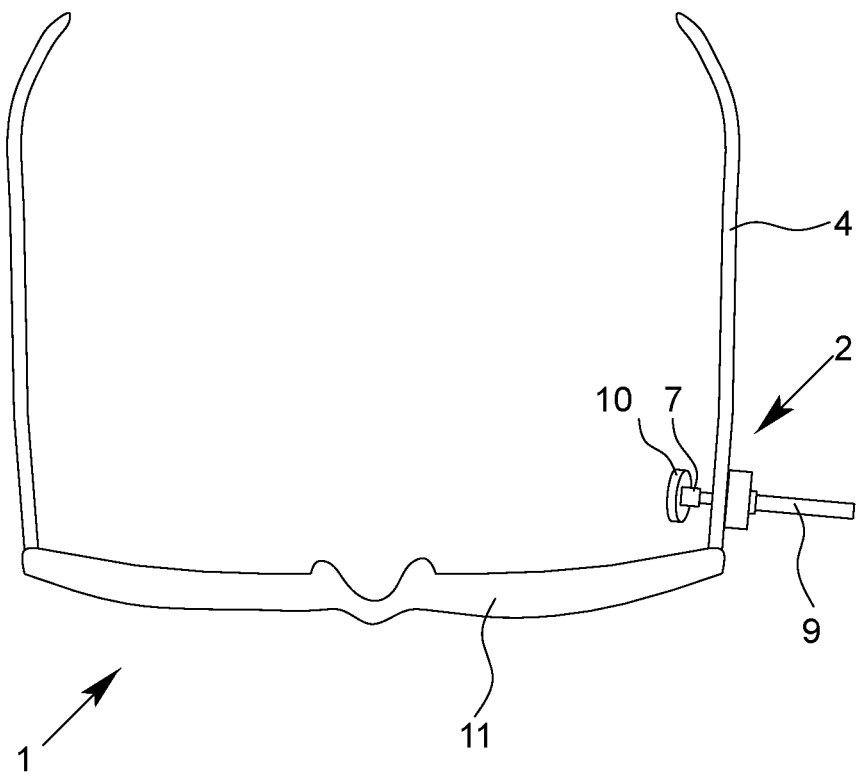
Figure 4:
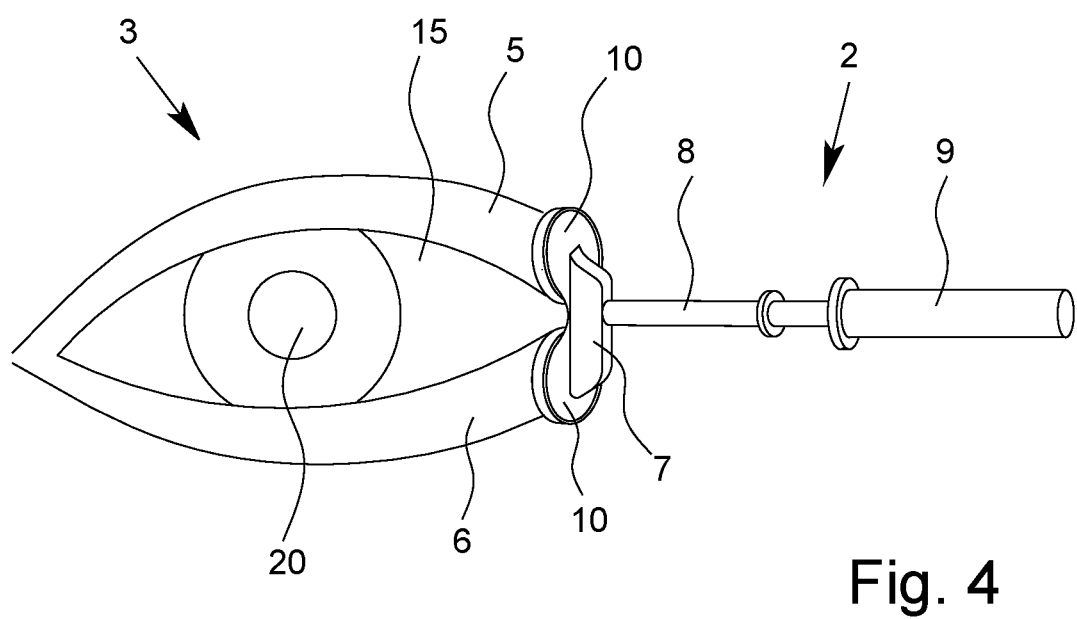
Figure 5:
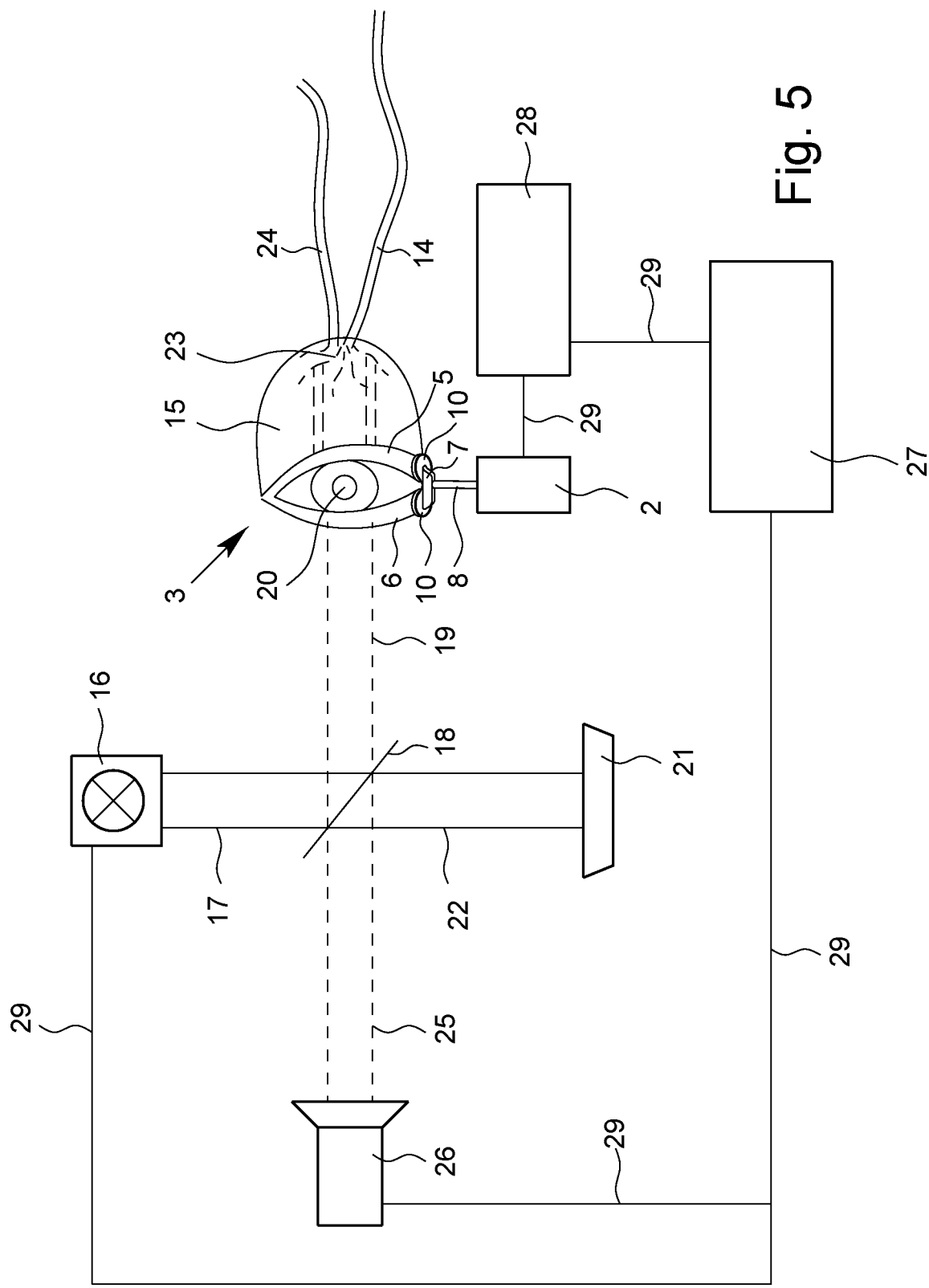
Figure 6:
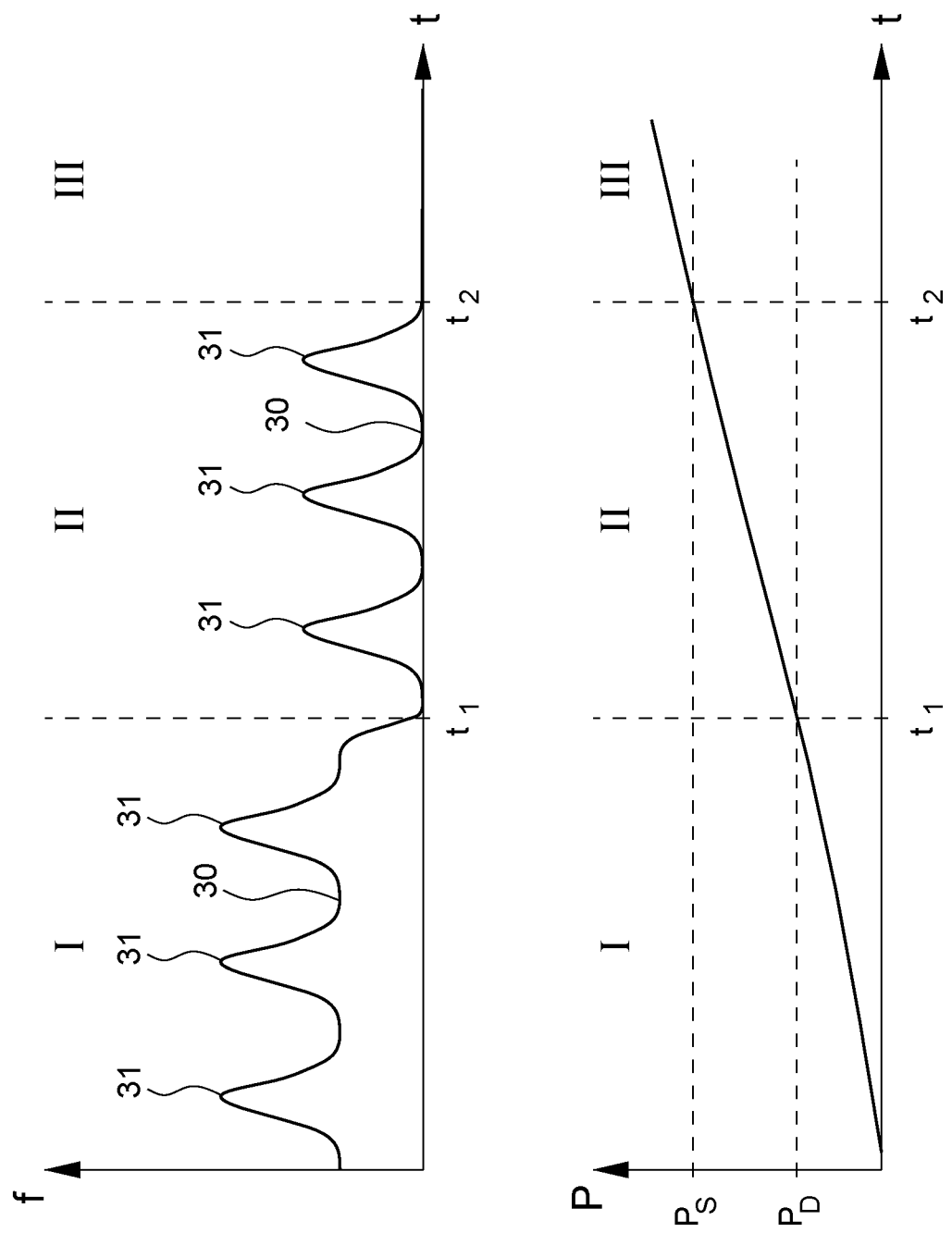
Figure 7:
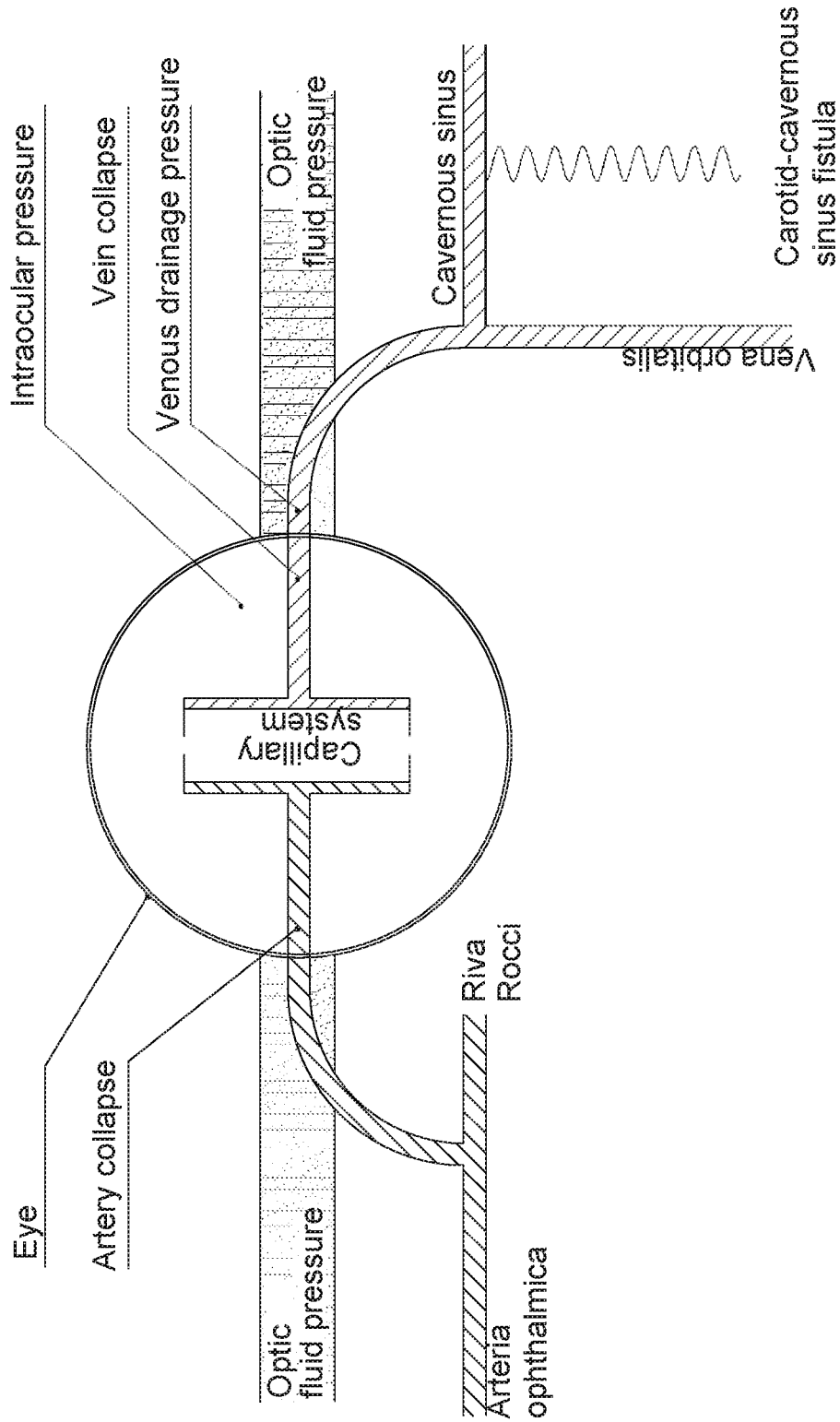
Figure 8:
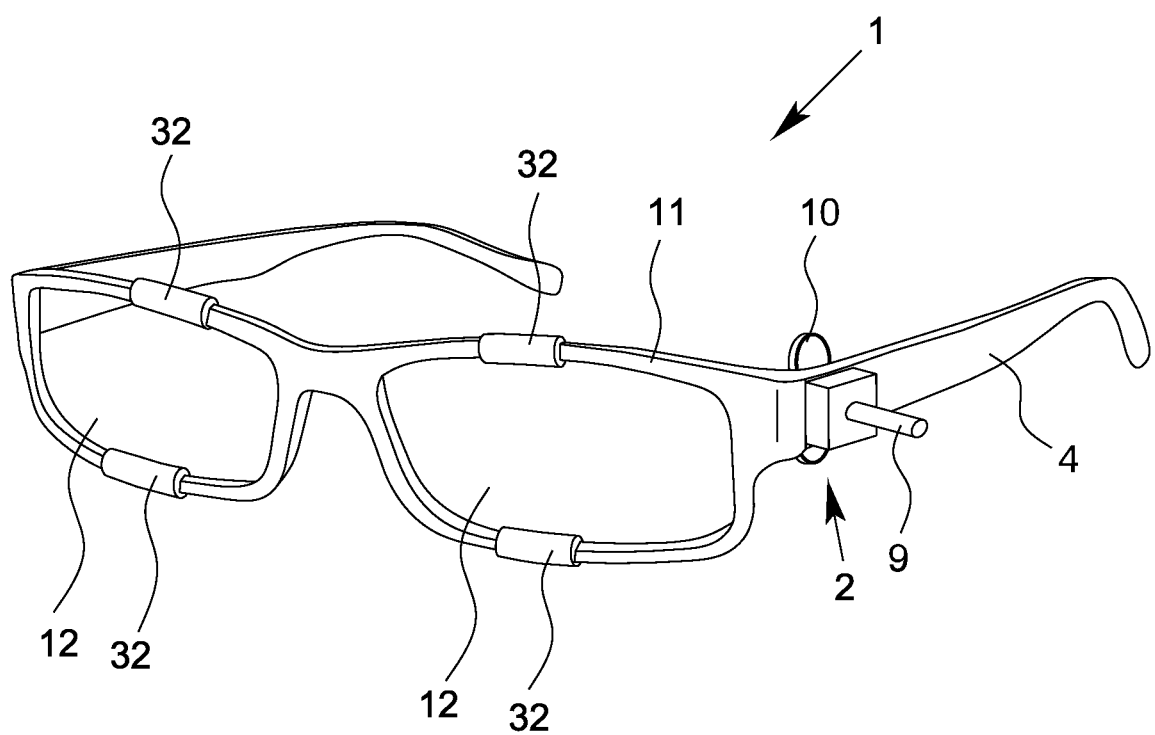
Figure 9:
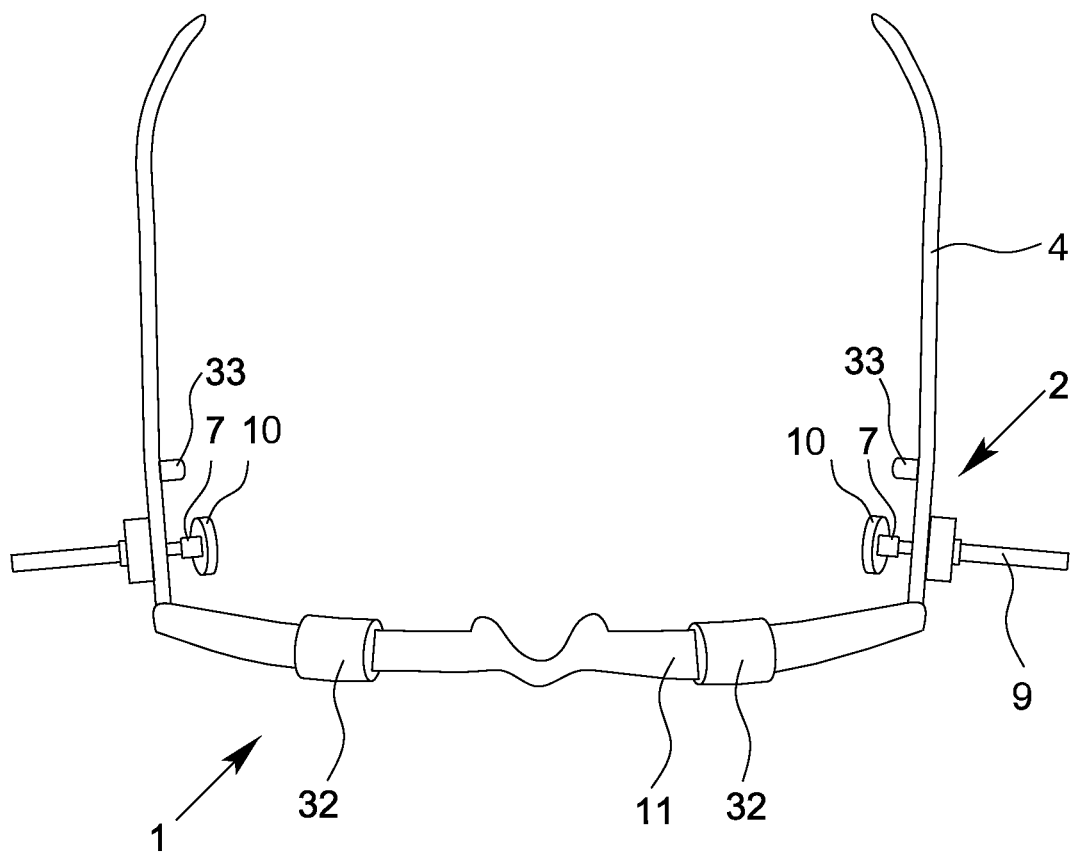
Figure 10:
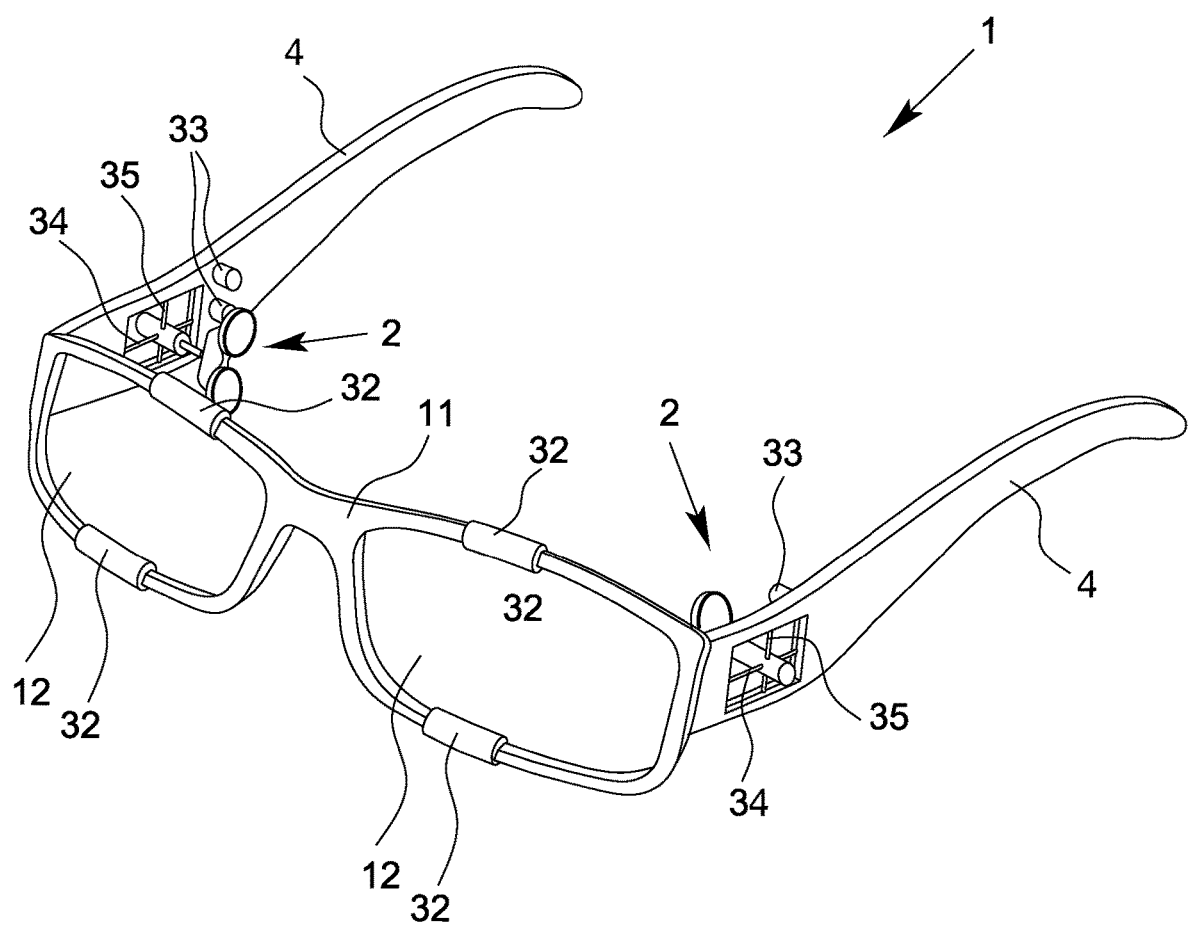

FIG. 1 shows a perspective schematic representation of a preferred embodiment of a holding device according to the invention seen diagonally from the front, FIG. 2 shows a perspective schematic representation of the holding device of FIG. 1 seen diagonally from the rear, FIG. 3 shows a schematic representation of the holding device of FIG. 1 in top view, FIG. 4 shows a schematic representation of a pressure generator during use, FIG. 5 shows a schematic representation of a preferred embodiment of an ophthalmodynamometry assembly according to the invention, FIG. 6 shows a schematic diagram representation of a typical time curve of the measured blood flow in a vessel of the eye and the pressure exerted on the eye, FIG. 7 shows a schematic representation showing the pressure compartments and the collapse locations of the central retinal vessels, FIG. 8 shows a perspective schematic representation of another preferred embodiment of a holding device according to the invention seen diagonally from the front, FIG. 9 shows a schematic representation of another preferred embodiment of a holding device according to the invention in top view, and FIG. 10 shows a perspective schematic representation of another preferred embodiment of a holding device according to the invention seen diagonally from the front.

FIGS. 1 to 3 show a holding device 1 according to the invention with a pressure generator 2. In the embodiment shown, the holding device 1 is designed as an eyeglass frame and can therefore be easily brought into position on the head of a person (not shown) in order to perform an ophthalmodynamometric measurement for a brief or a lengthy time. In this way, the pressure generator 2 is brought into an optimal position for an exertion of pressure on an eye 3 (not shown in FIGS. 1 to 3).

For this purpose, the pressure generator 2 is arranged on a holding element 4 or connected to a holding element 4. The holding element 4 in the present case is designed as an eyeglass arm, to which the pressure generator 2 is firmly connected. According to the invention, a releasable connection of the pressure generator 2 to the holding element 4 is also possible.

Alternatively or additionally, furthermore, the holding element 4 may be designed such that for its part it can be connected together with the pressure generator 2 to an object, such as otherwise present eyeglasses.

The exertion of pressure on the eye 3 by the pressure generator 2 occurs in particular, as shown in FIG. 4, across the upper eyelid 5 and/or the lower eyelid 6 of the eye 3 from a sideways direction. For this, the pressure generator 2 comprises a contact element 7, which in the present case is hinged to a piston rod 8, which is axially movable through a pneumatic cylinder 9, that is, in the application situation shown in FIG. 4, toward the eye 3 and in a direction away from the eye 3.

The contact element 7 further comprises two separate contact sections 10, respectively designed for positioning against the upper eyelid 5 and the lower eyelid 6. The contact elements 10 for their part may furthermore be hinged.

Alternatively or additionally to a pneumatic movement of the contact element 7, a movement can also be provided based on a purely mechanical, electromechanical, and/or hydraulic principle. This is especially important for a measurement during increasing pressure.

Moreover, the design of the contact sections 10 may differ from the form represented as a contact plate. Depending on the specific application, for example, a design as a knob and/or a plunger may also be suitable.

The exertion of pressure through the upper eyelid 5 and the lower eyelid 6 of the eye 3 occurs preferably in the region of the temporal angle of the eyelid. Such an exertion of pressure on the eye 3 during an ophthalmodynamometric examination only results in a slight increase in pressure in the retrobulbar space, whereas in other positions a measurement of the vascular pressure in the retrobulbar space would be falsified.

Furthermore, not individually shown in the drawing is a means whereby the pressure generator 2 is designed such that, upon reaching a set and/or settable maximum pressure on the eye 3, there is automatically no further pressure exerted by the pressure generator 2. This ultimately serves to protect the eye 3 against too great a mechanical strain, which in the extreme case might result in an injury or in general to damage in or at the eye 3.

In the simplest case, such a means can be realized by a mechanical stop, which restricts the axial movement of the piston rod 8 and thus that of the contact element 7 to a set maximum value. Alternatively or additionally to such a mechanical solution, the pressure exerted by the pressure generator 2 may also be detected by a pressure determination device (not shown), which upon reaching a set and/or settable maximum pressure switches off the operation of the pressure generator 2 and/or reverses the movement of the piston rod 8 and the contact element 7.

In the depicted embodiment of the holding device 1 according to the invention, this has further features normally provided for eyeglasses, yet they are not of fundamental importance for use as a holding device 1 for a pressure generator 2 during an ophthalmodynamometric measurement. However, the familiar eyeglass shape enhances the basic acceptance by the persons being examined to put on and use the holding device 1.

Moreover, the holding device 1 may also be designed such that, besides a firm fit of the holding device 1 on the head of the person and a reproducible positioning of the pressure generator 2 relative to the eye 3 being examined, means may also be integrated for correction of the person's vision, for example. For this purpose, the holding device 1 in the embodiment shown comprises a frame 11 surrounding two viewing windows 12, in which eyeglass lenses for vision correction or for filtering of light of a particular wavelength may be installed.

An ophthalmodynamometric measurement at the eye 3 of a person may be done by means of an ophthalmodynamometry assembly 13 according to the invention, which is shown in a preferred embodiment in FIG. 5. The depicted ophthalmodynamometry assembly 13 ultimately serves to perform a reliable determination of the occurrence of a vascular collapse of a blood vessel 14 of the eye 3. In principle, vascular collapse analysis is also conceivable in other sections of the eye.

For such a determination of the occurrence of a vascular collapse, pressure is first preferably exerted by the pressure generator 2, whose preferred design has already been explained, by means of the contact element 7 or the contact sections 10 of the contact element 7 indirectly on the eye 3 through its upper eyelid 5 and/or lower eyelid 6. Thanks to the pressure exerted from the sideways direction on the eye 3 in the region of the temporal angle of the eyelid, the eyeball 15 is not pressed into the eyeball socket (not shown), so that the tissue pressure in the orbita is not needlessly increased and a faulty measurement due to this is prevented.

In addition to the pressure generator 2, the ophthalmodynamometry assembly 13 comprises a measurement and evaluation device, which in turn may have a series of components as needed.

According to the invention, the measurement and evaluation device is designed for the indirect determination of the vascular collapse from a detected change in the blood flow of a blood vessel at the entrance to the eyeball 15 and/or at the exit from the eyeball 15.

In the preferred embodiment of the ophthalmodynamometry assembly 13 shown in FIG. 5, the measurement and evaluation device is designed to employ the method of optical coherence tomography (OCT angiography).

For this, the measurement and evaluation device comprises first of all a light source 16.

The light source 16 in the present instance emits light with a spectral composition making it possible for the light to penetrate the exposed tissue layers in the eye 3 at least for a certain distance. For this, the light source 16 may emit light in particular with a high spectral fraction in the infrared region. The light of the light source 16 should moreover have a relatively short coherence length in order to carry out the OCT. This means that the light used is relatively broadband. For example, a NIR LED is substantially more broadband than a NIR laser and it therefore has a considerably shorter coherence length. This may be necessary, since the tissue being examined has strong scattering. If a NIR laser were to be used, the scattering in the tissue might result in countless interferences, which might cause problems for evaluation with the detector.

The light of the light source 16 is now taken for the measurement as the primary beam 17 to a beam splitter 18, such as semi-transparent mirror. The beam splitter 18 now deflects the primary beam 17 as the incident measuring beam 19 onto the eye 3, into which the light given off by the light source 16 penetrates through the pupil 20 of the eye 3.

A portion of the primary beam 17, on the other hand, passes through the beam splitter 18 and arrives at a reflector 21, such as an ordinary mirror, from which the incident light is reflected back unchanged as reference beam 22.

In the eye 3, the papilla 23 in particular is illuminated, i.e., the region in which the optic nerve 24 enters into the eyeball 15. The principal supply vessels also enter into the eye 3 in this region. The incident light is backscattered by the tissue layers being examined. Due to the different travel time or travel distance of the light on account of the different structures in the illuminated tissue, the light of the measuring beam 19 departs from the coherence region with respect to the reference beam 22 in some regions. The light backscattered from the eye 3 as the outgoing measuring beam 19 once again arrives at the beam splitter 18, through which it passes, becoming combined with the reference beam 22 reflected or diverted by the beam splitter 18 into a resulting beam 25.

In the resulting beam 25, interference occurs in regions across its cross section between the light of the measuring beam 19 and the reference beam 22. The interference pattern is dependent on the structures illuminated in the eye 3 with the measuring beam 19. By means of an imaging optics (not shown), the light of the measuring beam 19 or the resulting beam 25 can be directed to a detection device 26. The focal length of the imaging optics is shown such that a particular tissue layer in the eye 3 will be imaged. Thanks to the imaging plane passing through a tissue volume, the tissue volume can be registered layer by layer as a three-dimensional tomogram. The imaging optics, which may consist of a lens system, focuses the IR light on different tissue structures in succession. A two-dimensional image is produced for each tissue layer. Taken together, one ultimately derives a three-dimensional volume image.

Furthermore, the phase of the light backscattered as the measuring beam 19 from the tissue structures in the eye 3 is also influenced by the movement of an imaged object. For this reason, the blood flow or the flow movement of the blood in a vessel 14 can be detected in reliable manner. If a suspension of the blood flow in the vessel 14 can be detected, this is a sign of the presence of a vascular collapse of the respective vessel 14. This ultimately constitutes the basic principle of the present invention.

For this purpose, the detection device 26 is preferably designed to record a two-dimensional image, especially as a camera or as a sensor array, and basically preferably resembles known detection devices for OCT measurements, which are already in use for example as a fundus camera.

The data recorded by the detection device 26 or the picture taken by the detection device 26 can be visualized and/or digitized and further processed in this form and/or be stored in memory.

For processing the data of the detection device 26, the measurement and evaluation device comprises an evaluation unit 27. The evaluation unit 27 may be in particular a computer, an electronic circuit or another data processing device. In particular, the evaluation of the data of the detection device 26 can be performed by corresponding software.

For the determination of a vascular collapse in a vessel 14 at the eye 3 according to the invention, the fundus is repeatedly recorded at short time intervals, in particular in the region of the papilla, with the above-described apparatus. From the data so acquired, the blood flow in the vessel 14 can be obtained in particular, at least in a qualitative manner.

The pressure exerted by the pressure generator 2 on the eye 3 is now steadily increased. If, as a result of the pressure exerted by the pressure generator 2, the ambient pressure in the region of the vessel 14 exceeds the vascular pressure in its interior, a collapse of the vessel 14 will occur. During the vascular collapse, the blood flow is suspended in the interior of the vessel 14. This can be ascertained in the form of a change in the image registered by the detection device 26 or the data registered by the detection device 26, and it can be appropriately evaluated and stored in memory by the evaluation unit 27.

Moreover, the evaluation unit 27 can store the pressure exerted on the eye 3 by means of the pressure generator 2 at the moment of the vascular collapse. The pressure exerted by the pressure generator 2 on the eye 3 can be dictated, read out, and/or determined indirectly by means of a pressure determination device (not individually shown).

Thanks to an appropriate calibration, the vascular pressure can be determined from the pressure exerted by the pressure generator 2 on the eye 3 at the moment that vascular collapse occurs. In particular, a reliable conclusion as to the intracranial pressure can also be drawn in particular by a measurement of the venous vascular pressure. In particular, the determination of a venous vascular collapse which is necessary for this is only possible in an unreliable manner, if at all, by means of known visual methods.

For the automatic or at least partly automated performance of the above-described ophthalmodynamometric method, the ophthalmodynamometry assembly 13, as in the form depicted in FIG. 5, may comprise a control device 28. In this case, the control device 28 serves in particular for control of the pressure generator 2 in that the pressure exerted by the pressure generator 2 on the eye 3 is specified or set by the control device 28.

Preferably, the control device 28 is connected by a back channel to a pressure determination device, by means of which the pressure actually exerted at the time on the eye 3 can be detected. In this way, a targeted regulation of the pressure generator 2 in relation to the pressure exerted on the eye 3 by the control device 28 is possible.

The control device 28 can also control the detection device 26 in relation to the data acquisition, especially in regard to the relevant frequency of the data acquisition for the temporal resolution of the measurement. Furthermore, a control of the light source 16 and of the evaluation unit 27 is also possible according to the invention.

The interaction of the individual components of the measurement and evaluation device is made possible in particular by a linking of the components through data and control lines 29. Of course, the data/control lines 29 need not be designed as a conductive link, but rather may also be realized for example by a wireless transmission of data and/or control signals.

In the ophthalmodynamometry assembly 13 according to the invention, the pressure generator 2 is connected in particular to a holding device 1 according to the invention, preferably in a basic configuration according to the representation of FIGS. 1 to 3, and is held by this in an optimal position relative to the eye 3 to be examined.

FIG. 6 is a schematic depiction of an exemplary time curve of data plotted during a measurement to determine the occurrence of a vascular collapse. The upper diagram in FIG. 6 corresponds to the time curve of the blood flow f obtained from the data of the detection device 26. An absolute quantification of the blood flow f is not absolutely necessary in this case.

The lower diagram in FIG. 6 shows, in a time scale identical to the upper diagram, the curve of the pressure P present in the vicinity of the vessel 14 as a result of an increasing exertion of pressure by the pressure generator 2 on the eye 3, which can be determined by calibration from the pressure exerted on the eye 3 from the outside.

As can be seen, starting from a baseline pressure value, the pressure P on the vessel 14 increases steadily on account of the increasing pressure exerted by the pressure generator 2 on the eye 3. The blood flow f in the vessel 14 at first alternates between a plateau 30, reflecting a certain baseline flow of blood in the vessel 14, and pulses 31 going beyond the plateau 30. The pulses 31 indicate a faster blood flow f in the vessel 14 due to the pumping activity of the heart.

Now, if the ambient pressure P at the vessel 14 increases at time point $t_1$ to a value corresponding to the diastolic vascular pressure $P_D$, the blood flow f in the region of the plateau 30 between the pulses 31 drops essentially to zero. Thus, the blood flow f is suspended between the pulses 31. The vascular pressure is accordingly no longer large enough to withstand the ambient pressure P in the area of the vessel 14, so that the vessel 14 collapses. Due to the pumping activity of the heart, however, the vascular pressure is briefly increased in a pulse-like manner such that the ambient pressure P is briefly exceeded, so that the vascular collapse is temporarily cancelled and the blood continues to flow in the vessel 14 during this time.

If the ambient pressure is further increased as a result of an increasing exertion of pressure on the eye 3 by the pressure generator 2, the ambient pressure P on the vessel 14 at time point $t_2$ will correspond to the systolic vascular pressure $P_S$. After exceeding this pressure, the vascular pressure is no longer able, even during the pumping activity of the heart, to expand the collapsed vessel. Accordingly, as of time point $t_2$ the blood flow f comes entirely to a halt, as shown by the upper diagram in FIG. 6.

The time points $t_1$, $t_2$ for reaching the characteristic vascular pressures $P_D$, $P_S$ thus partition the time curve of the acquired data into three sections I, II, III. In the first section I, the ambient pressure P on the examined vessel 14 is less than the diastolic vascular pressure $P_D$. Accordingly, an unhindered blood flow is possible. In the second section II, the ambient pressure P on the vessel 14 is between the diastolic vascular pressure $P_D$ and the systolic vascular pressure $P_S$. A blood flow f can accordingly be measured only briefly during the pumping activity of the heart in the form of pulses 31. In the third section III, finally, the ambient pressure P on the vessel 14 is greater than the systolic vascular pressure $P_S$ which is present during the pumping activity of the heart. Accordingly, a complete suspension of the blood flow is detected.

The transitions between the sections I, II, III are clearly identifiable with the aid of the time curve of the blood flow f, and establish characteristic time points $t_1$ and $t_2$. Given an appropriate calibration, finally, characteristic vascular pressure values in the form of the diastolic vascular pressure $P_D$ and the systolic vascular pressure $P_S$ can be determined from the ambient pressure P on the vessel 14 which is present at the time points $t_1$ and $t_2$.

FIG. 7 is a schematic representation of the pressure compartments and the collapse locations of the central retinal vessels.

Unlike the central artery (central retinal artery), the venous system (also the central vein or central retinal vein) is a low-pressure system. In most instances, the collapse behavior of the central vein will be expected to be similar to that of the central artery. Analogous conditions apply here for the vascular collapse as in the case of the central artery.

According to clinical observations, special forms of vascular collapse may be anticipated here, unlike the arterial collapse. Even so, a vascular collapse can also be detected here with the aid of OCT flow analysis.

Since intracranial pressure is largely responsible for venous pressure, a measurement of intracranial pressure is also possible with the aid of venous pressure. The establishing of a spontaneous venous collapse with the aid of the collapse vessel analysis is itself sufficient to determine a non-increased intracranial pressure, even without a dynamometric method. In particular, the dynamometry as described above can only be carried out in cases in which no spontaneous venous collapse is present.

FIG. 8 shows another preferred embodiment of the holding device 1 according to the invention. In the example shown there, the holding device 1 corresponds in its basic construction to the exemplary embodiment of FIG. 1. However, in the present instance, the holding device 1 further comprises an adjusting device 32, by means of which its size can be changed, in the present case with regard to its width.

In the present representation, multiple adjusting devices 32 are provided in the frame 11 of the holding device 1. However, the mounting will depend ultimately on the particular application and can basically be realized in any desired location, such as centrally.

In the example shown, the adjusting device 32 is configured as a sleeve-like element, in which portions of the frame 11 are arranged movably, especially telescopically, so that the eyeglass frame-like holding device 1 can be altered for adaptation to a particular head shape by pulling and pushing it along its width, with different settings being fixed by click stops (not shown in detail) in the interior of the adjusting device 32. Alternatively or additionally, a configuration of the adjusting device 32 as a bow, a rail system, and/or an adjusting screw may also be provided.

Thanks to the mounting of the adjusting devices 32 in the area of the frame 11, these are easily accessible and thus enable a problem-free adjusting of the holding device 1 to the shape of the head of the wearer.

FIG. 9 shows another preferred exemplary embodiment of the holding device 1 according to the invention, being designed in this representation likewise as an eyeglass frame. In departure from the embodiment shown in FIG. 3, however, the holding device 1 in the present instance has pressure generators 2 on both sides, i.e., on both holding elements 4 designed as eyeglass arms. Such a symmetrical construction enables an examination of both eyes 3 with little adjustment effort, especially with no time-consuming switching of the pressure generator 2 from one side of the head to the other and without the need to keep a second holding device 1 ready for the examination of the second eye 3.

Moreover, when pressure is exerted on the eye 3 by one of the pressure generators 2, given an appropriate positioning of the other respective pressure generator 2 on the bone, especially at the rim of the eye socket, a correspondingly great counterpressure can be produced, so that the pressure exerted acts on the eye 3 only in the desired manner, without shifting the holding device 1 against the direction of force exertion by the pressure generator 2, i.e., against the movement of the piston rod 8 in particular.

In the exemplary embodiment of FIG. 9, moreover, abutment elements 33 are shown for placement against the cranial bone, preferably the orbital rim. The abutment elements 33 serve in the present case as a static abutment in order to absorb the counterforce during the exertion of pressure on the eye 3 by means of the pressure generator 2 mounted opposite the abutment element 33.

One or more abutment elements 33 may be provided independently of a symmetrical design of the holding device 1 with pressure generators 2 on both sides, but also in combination with them in a mutually complementary manner, as shown in the example of FIG. 9.

FIG. 10 shows a further exemplary embodiment of the holding device 1 according to the invention. In this example as well, two pressure generators 2 are provided on both sides. Apart from this, the particularity of this preferred embodiment is that the pressure generator 2 is movably mounted and can be moved by a first displacement device 34 in the distal direction. Furthermore, independently of this, it can be moved by a second displacement device 35 in the vertical direction. This allows an exact positioning of the pressure generator 2 relative to the corresponding eye 3, so that contact of the eye 3 with the contact element 7 or with the contact sections 10 occurs at the optimal position, preferably at the temporal angle of the eyelid through the upper eyelid 5 and/or the lower eyelid 6.

By means of the displacement devices 34, 35, furthermore, the pressure generator 2 can be moved into a position in which it can optimally exert a counterforce to the exerted pressure of the oppositely situated pressure generator 2 in the sense of a dynamic abutment. A suitable location for this, as described above, is on the rim of the eye socket in the region of the eyeball equator.

Moreover, according to the invention, an adjustment of the angle of the pressure generator 2 with respect to the eye 3 can be performed. For reasons of clarity of the drawing, however, a corresponding device, such as a joint, is not shown in detail.

The presented exemplary embodiments serve merely for the exemplary illustration of the features of preferred embodiments of the holding device 1 according to the invention, especially in the function of a dynamometry assembly. Represented features may be realized in any desired combination and independently of each other.

In particular, the holding device 1 may be designed other than as an eyeglass frame, or a different kind of eyeglass frame than the one shown can be used.

Moreover, not specifically shown is a data transmission device in the form of a data transmission interface. In particular, in one preferred embodiment as a wireless data transmission interface, this may also be integrated into the holding device 1, in the present examples preferably into the frame 11 or into a holding element 4.

LIST OF REFERENCE SYMBOLS

| | |
|---|---|
| 1 | Holding device |
| 2 | Pressure generator |
| 3 | Eye |
| 4 | Holding element |
| 5 | Upper eyelid |
| 6 | Lower eyelid |
| 7 | Contact element |
| 8 | Piston rod |
| 9 | Pneumatic cylinder |
| 10 | Contact section |
| 11 | Frame |
| 12 | Viewing window |
| 13 | Ophthalmodynamometry assembly |
| 14 | Blood vessel |
| 15 | Eyeball |

| | |
|---|---|
| 16 | Light source |
| 17 | Primary beam |
| 18 | Beam splitter |
| 19 | Measuring beam |
| 20 | Pupil |
| 21 | Reflector |
| 22 | Reference beam |
| 23 | Papilla |
| 24 | Optic nerve |
| 25 | Resulting beam |
| 26 | Detection device |
| 27 | Evaluation unit |
| 28 | Control device |
| 29 | Data/control line |
| 30 | Plateau |
| 31 | Pulse |
| 32 | Adjusting device |
| 33 | Abutment element |
| 34 | Displacement device (distal) |
| 35 | Displacement device (vertical) |
| t | Time |
| $t_1$ | Time point |
| $t_2$ | Time point |
| f | Blood flow |
| P | Pressure |
| $P_D$ | Diastolic pressure |
| $P_S$ | Systolic pressure |
| I | First section |
| II | Second section |
| III | Third section |

The invention claimed is:

1. A method for determining the occurrence of a vascular collapse of a blood vessel in or at an eye at one or more of an entrance to an eyeball and at an exit from the eyeball, comprising: determining whether the vascular collapse has occurred from a directly measured temporal change of blood flow within the blood vessel; wherein one or more of: the blood flow is directly measured by an optical method, the optical method being time-resolved optical coherence tomography (OCT), the blood flow is measured by scanning laser Doppler flowmetry (SLDF), and a the blood flow is directly measured by laser speckle flowmetry.

2. The method according to claim 1, further comprising one or more of:
   exerting pressure on the eye until achieving a vascular collapse, and
   exerting pressure on the eye when no spontaneous vascular collapse is present.

3. The method according to claim 2, wherein one or more of:
   the exertion of pressure on the eyeball is done laterally and/or indirectly, via an upper eyelid and/or a lower eyelid of the eye, in the region of the temporal angle of the eyelid, and
   the pressure exerted on the eye is specified, measured, determined, and/or visualized one or more of manually and automatically by a measurement and evaluation device.

4. The method according to claim 1, wherein vascular pressure in the blood vessel is determined from pressure exerted on the eye upon occurrence of the vascular collapse.

5. The method according to claim 1, wherein there is an undulating exertion of pressure on the eye.

6. The method according to claim 1, wherein a wireless and/or bidirectional data transmission occurs between a pressure generator and a measurement device, wherein a transmission of control data and/or of measurement data including a pressure value, occurs.

7. The method according to claim 1, wherein the blood flow measurement is taken in an interior of the blood vessel.

8. A holding device comprising:
   a pressure generator; and
   a holding element, wherein the pressure generator is held on the holding element and configured to exert pressure on an eye by the pressure generator, this pressure being applied from a sideways direction through one or more of an upper eyelid and a lower eyelid the pressure being applied in a region of a temporal angle of the eyelid of the eye.

9. The holding device according to claim 8, wherein one or more of the holding device is wearable eyeglasses, and/or the holding element is an eyeglass arm or adapted for connection to an eyeglass arm.

10. The holding device according to claim 8, wherein one or more of:
    the pressure generator comprises a contact element, that is mechanically, hydraulically, and/or pneumatically movable as the contact element being a knob, plunger, or contact plate, configured for placement against the eye, wherein one or more of the contact element is hinged and comprises a plurality of separate contact sections, wherein at least two contact sections are configured for placement against the eye, and
    the pressure generator is configured so that upon reaching a specifiable pressure on the eye, the pressure generator automatically performs no further pressure increase.

11. The holding device according to claim 10, wherein the contact element is interchangeable.

12. The holding device according to claim 10, wherein at least one contact section has a convex curvature.

13. The holding device according to claim 8, further comprising an adjusting device adapted to altering one or more of a shape and size of the holding device.

14. The holding device according to claim 8, wherein the holding element has at least one displacement device for one or more of a vertical and a distal displacement of the pressure generator.

15. The holding device according to claim 14, wherein the displacement device includes a position sensor, and/or is one or more of electromotorized, pneumatically and/or hydraulically operable and/or remote controllable.

16. The holding device according to claim 8, wherein at least one abutment element is provided for placement against a contact point on a bone.

17. The holding device according to claim 16, wherein the abutment element is one or more of: removable, interchangeable, displaceable on the holding device and adjustable in size.

18. The holding device according to claim 8, wherein a wireless data transmission interface is provided, wherein the data transmission interface provides for bidirectional data transmission and/or for transmission of control data and/or measurement values of a pressure sensor, and wherein the data transmission interface couples the holding device to a measurement assembly, the measurement assembly being one or more of an optical coherence tomography assembly, a scanning laser Doppler flowmetry assembly, and a laser speckle flowmetry assembly.

19. The holding device according to claim 8, further comprising a pressure determination device including a pressure sensor, wherein the pressure determination device is decoupled from the pressure generator with respect to the pressure generation.

20. A method for determining outflow resistance for aqueous humor of an eye comprising:

measuring an internal pressure of the eye,
- inducing an exertion of pressure on the eye by a dynamometry assembly that includes a holding device with a pressure generator and a holding element, wherein the pressure generator is held on the holding element to exert pressure on an eye by the pressure generator from a sideways direction through an upper eyelid and/or a lower eyelid in a region of a temporal angle of the eyelid of the eye,
- measuring the internal pressure of the eye after the exertion of pressure, and
- determining a value for the outflow resistance from a difference between the measured internal pressures.

* * * * *